United States Patent
Shen

(10) Patent No.: US 8,815,307 B2
(45) Date of Patent: Aug. 26, 2014

(54) PROCESS FOR PRODUCING POROUS POLYMER MASTERBATCH AND FIBER THEREOF HAVING ANTI-BACTERIAL AND ODOR ELIMINATING FUNCTIONS

(75) Inventor: Kuen-Chin Shen, Taipei (TW)

(73) Assignee: Colotex Industrial Co., Ltd., Taipei (TW)

( * ) Notice: Subject to any disclaimer, the term of this patent is extended or adjusted under 35 U.S.C. 154(b) by 1037 days.

(21) Appl. No.: 12/347,359

(22) Filed: Dec. 31, 2008

(65) Prior Publication Data

US 2010/0166817 A1    Jul. 1, 2010

(51) Int. Cl.
  *A61K 36/00*    (2006.01)
  *A01N 65/00*    (2009.01)
  *A01N 25/34*    (2006.01)

(52) U.S. Cl.
  CPC ............... *A01N 25/34* (2013.01); *A01N 65/00* (2013.01)
  USPC ........................................................ 424/725

(58) Field of Classification Search
  None
  See application file for complete search history.

(56) References Cited

U.S. PATENT DOCUMENTS

| | | | |
|---|---|---|---|
| 5,466,455 A | 11/1995 | Huffstutler, Jr. et al. | |
| 6,287,550 B1 * | 9/2001 | Trinh et al. | 424/76.6 |
| 7,422,759 B2 * | 9/2008 | Kepner et al. | 424/618 |
| 2004/0247654 A1 | 12/2004 | Asmus et al. | |

FOREIGN PATENT DOCUMENTS

| | | |
|---|---|---|
| CN | 19972039895 | 2/1999 |
| CN | 20022044729 | 10/2003 |
| CN | 20091131397 | 9/2009 |
| JP | 2007283206 A * | 11/2007 |
| WO | WO 0290025 A1 * | 11/2002 |

OTHER PUBLICATIONS

Rujitanaroj et al. Preparation of Ultrafine Poly(ethylene oxide)/Poly(ethyleneglycol) Fibers Containing Silver Nanoparticles as Antibacterial coating. Proceedings of the 2nd IEEE International Conference on Nano/Micro Engineered and Molecular Systems. Jan. 16-19, 2007, Bangkok, Thailand.*
European Search Report for Application No. 09173905.2-2115; date of completion of Search Report, Mar. 11, 2010.

* cited by examiner

*Primary Examiner* — Amy L Clark
(74) *Attorney, Agent, or Firm* — WPAT, P.C.; Anthony King; Kay Yang

(57) ABSTRACT

A process for producing porous polymer masterbatch having anti-bacterial and odor eliminating functions, wherein said fiber contains materials such as porous natural mineral kieselguhr or active carbon, can absorb and eliminate odor such as stink of sweat and the like discharged from the human body, has functions of sterilization, anti-bacterial, anti-mold, and the like. Pores of the natural mineral kieselguhr or active carbon contain organic Chinese herbal medicine and inorganic anti-bacterial minerals, wherein all of such organic Chinese herbal medicine and inorganic anti-bacterial minerals have functions of anti-bacterial, anti-fungal and the like, can eliminate effectively odor or reduce substantially stink, and can be applied extensively in various fabrics, clothes and ornaments or other goods.

3 Claims, 4 Drawing Sheets

PROCESS FOR PRODUCING POROUS POLYMER MASTERBATCH AND FIBER THEREOF HAVING ANTI-BACTERIAL AND ODOR ELIMINATING FUNCTIONS

BACKGROUND OF THE INVENTION

1. Field of the Invention

The invention relates to a process for producing porous polymer masterbatch and fiber thereof that have anti-bacterial and odor eliminating functions, and in particular, to a process for producing anti-bacterial and odor eliminating polymer masterbatch and fiber thereof containing organic or inorganic materials.

2. Description of the Prior Art

As the demand for a modern hygienic life increases, anti-bacterial products have gradually received more welcome from consumers. This trend extends to the textile industry and has resulted into considerable progress in the production of anti-bacterial fibers and clothing and other daily use articles.

Anti-bacterial agent used in the anti-bacterial fiber can be divided generally into two types, namely, an organic anti-bacterial agent, and an inorganic anti-bacterial agent. One of the organic anti-bacterial agents is quaternary ammonium salt. Unfortunately, quaternary ammonium salt has poor heat resistance and can not be used in the process for making plastics or fiber spinning products.

On the other hand, an inorganic anti-bacterial agent is a carrier (for example zeolite) containing metal ions (for example $Ag^+$, $Zn^{2+}$, $Cu^{2+}$), or certain types of nano-scale metal particles (for example nano-scale silver particles), and both are considered as effective particles in the following description.

Silver has a well-accepted anti-bacterial effect. In general, an antibiotic can kill approximately six different types of bacteria, while silver can kill about 600 types of bacteria. In addition, silver is a non-toxic substance, and therefore silver is used extensively and has a long history. Furthermore, through nanotechnology techniques, silver particles become more active and their anti-bacterial function is enhanced, thereby promoting the quality of the home environment and personal hygiene. Aqueous solutions containing silver ions released from both nano-scale silver granules and nanometer silver has remarkable anti-bacterial effect. Under the circumstance of multiple dilutions, nanometer silver still has an inhibition efficiency of 99.99% against *Escherichia coli, Staphylococcus aureus, Sarmonella, Pseudomonas aeruginosa* and the like. The principal cause of this resides in the biological action that silver has itself. Active silver ions can attract the sulfhydryl group on the enzymatic protein in the bacteria and causes these groups to quickly bind with each other, thereby rendering the enzymes containing sulfhydryl groups to lose activity and hence kill the bacteria.

A traditional process for using silver ion to produce fiber comprises immersing fiber in an organic anti-bacterial agent so as to adhere a carrier or nanometer silver particle on the surface of the fiber. In such traditional processes, effective particles in the anti-bacterial inorganic solvent may be easily washed off, and at the same time, may easily induce an allergic response in the user. Another process for producing anti-bacterial fiber comprises mixing an inorganic anti-bacterial agent and polyester, and then drawing the mixture thus-obtained into fibers containing effective particles. In such a process for making anti-bacterial fiber, most of the anti-bacterial materials are embedded within the fiber, and hence the anti-bacterial and odor eliminating functions are unable to be exhibited. Furthermore, part of the anti-bacterial material exposed on the outside of the fiber might lose its anti-bacterial and odor eliminating functions after washing or dying and finishing due to binding with chlorine, sulfur and the like.

In view of the foregoing, conventional techniques mentioned above still have many disadvantages, poorly designed and needs to be improvement.

The inventor had learned of the various disadvantages and shortcomings derived from such conventional techniques described above, and had thought to improve and innovate, and finally, after studying intensively for many years, has developed a process for producing porous polymer masterbatch and fiber thereof that have anti-bacterial and odor eliminating functions according to the invention.

SUMMARY OF THE INVENTION

One object of the invention is to provide a process for producing porous polymer masterbatch and fiber thereof that have anti-bacterial and odor eliminating functions, for the purpose of reducing lost particles in the anti-bacterial inorganic solvent, which tend to be washed off easily, and hence tend to lower the anti-bacterial effect as well as lead to potential unknown effects on the ecological equilibrium of the environment.

Another object of the invention is to provide a process for producing porous polymer masterbatch and fiber thereof that have anti-bacterial and odor eliminating functions, characterized in that the inventive process can improve the previous conventional process for making anti-bacterial fiber; where in the conventional process, an inorganic anti-bacterial agent is mixed in a polymer and then the resulted mixture is drawn to form fiber containing fine nanometer particles, and in such conventional process for making anti-bacterial fiber, the nanometer particles are difficult to be dispersed homogeneously in the fiber, and further, most of the nanometer particles are embedded within the fiber, so that its anti-bacterial effect can not function effectively.

Still another object of the invention is to provide a process for producing porous polymer masterbatch and fiber thereof that have anti-bacterial and odor eliminating functions, characterized in that wide and diverse materials can be used, and has a wide spectrum of anti-bacterial and anti-fungal effects.

The process for producing porous polymer masterbatch and fiber thereof that have anti-bacterial and odor eliminating functions comprises: step 1, grinding kieselguhr or active carbon into micro-particles; step 2, immersing said micro-particles obtained in step 1 in an organic Chinese herbal medicine and inorganic anti-bacterial minerals and polyvinyl alcohol with constant stirring; step 3, air-drying micro-particles thus-obtained in step 2, and dry-grinding further the dried micro-particles into finer particles suitable for drawing and to be dispersed homogeneously in a solution; step 4, carrying out a esterification reaction for binding monomer to form an anti-bacterial polyester masterbatch; and/or step 5, producing the polyester masterbatch formed in step 4 into anti-bacterial polyester fiber by cold grain spin-drawing technique.

BRIEF DESCRIPTION OF THE DRAWINGS

These features and advantages of the present invention will be fully understood and appreciated from the following detailed description of the accompanying drawings, wherein.

DETAILED DESCRIPTION OF THE PREFERRED EMBODIMENT

For understanding further the objects, characteristics and effects of the invention, the following non-limiting examples will be illustrated in conjunction with the accompanied drawings below.

Figure 1:
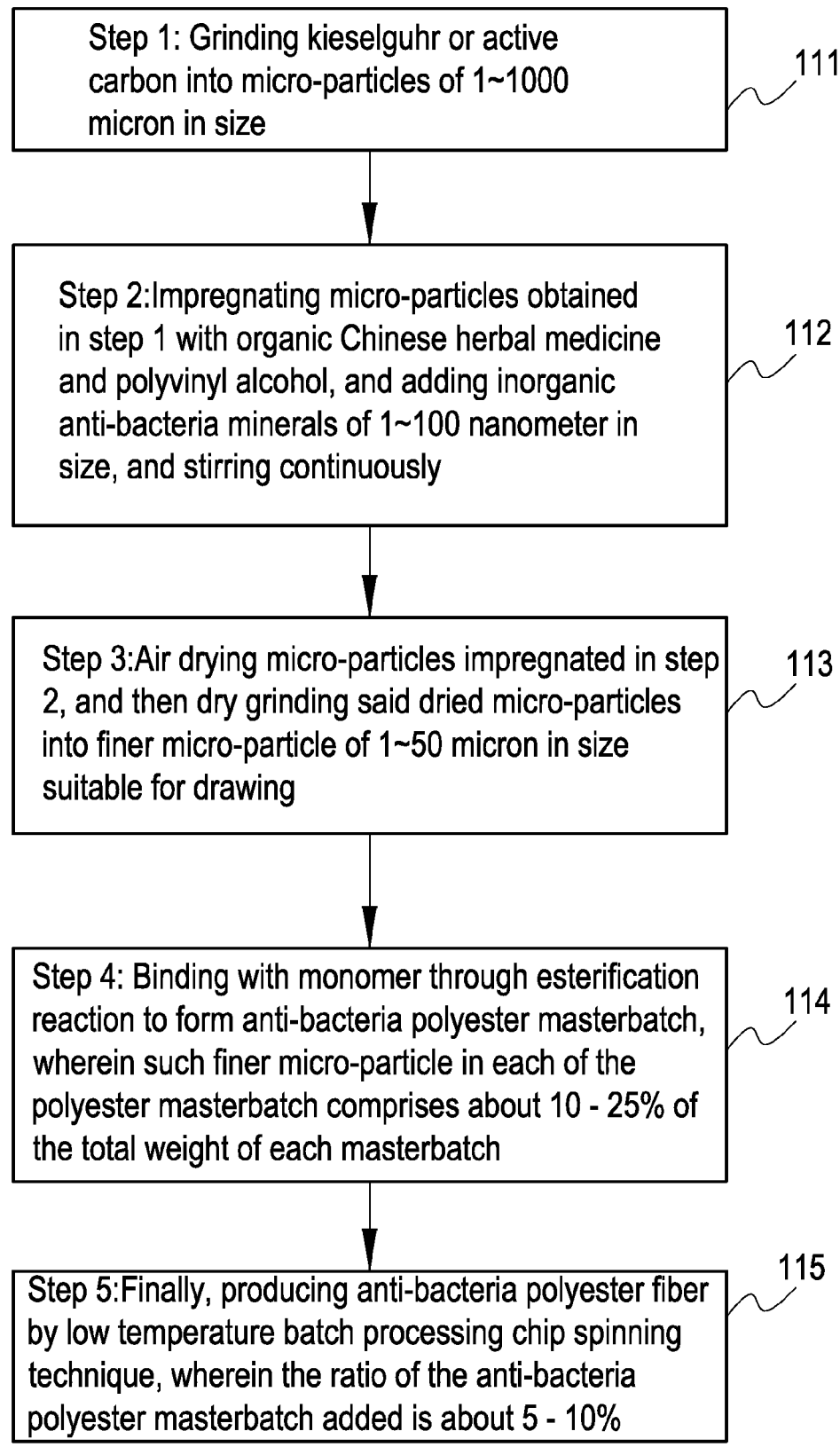
FIG. 1 shows the flow chart for carrying out the process according to the invention.
Figure 2:
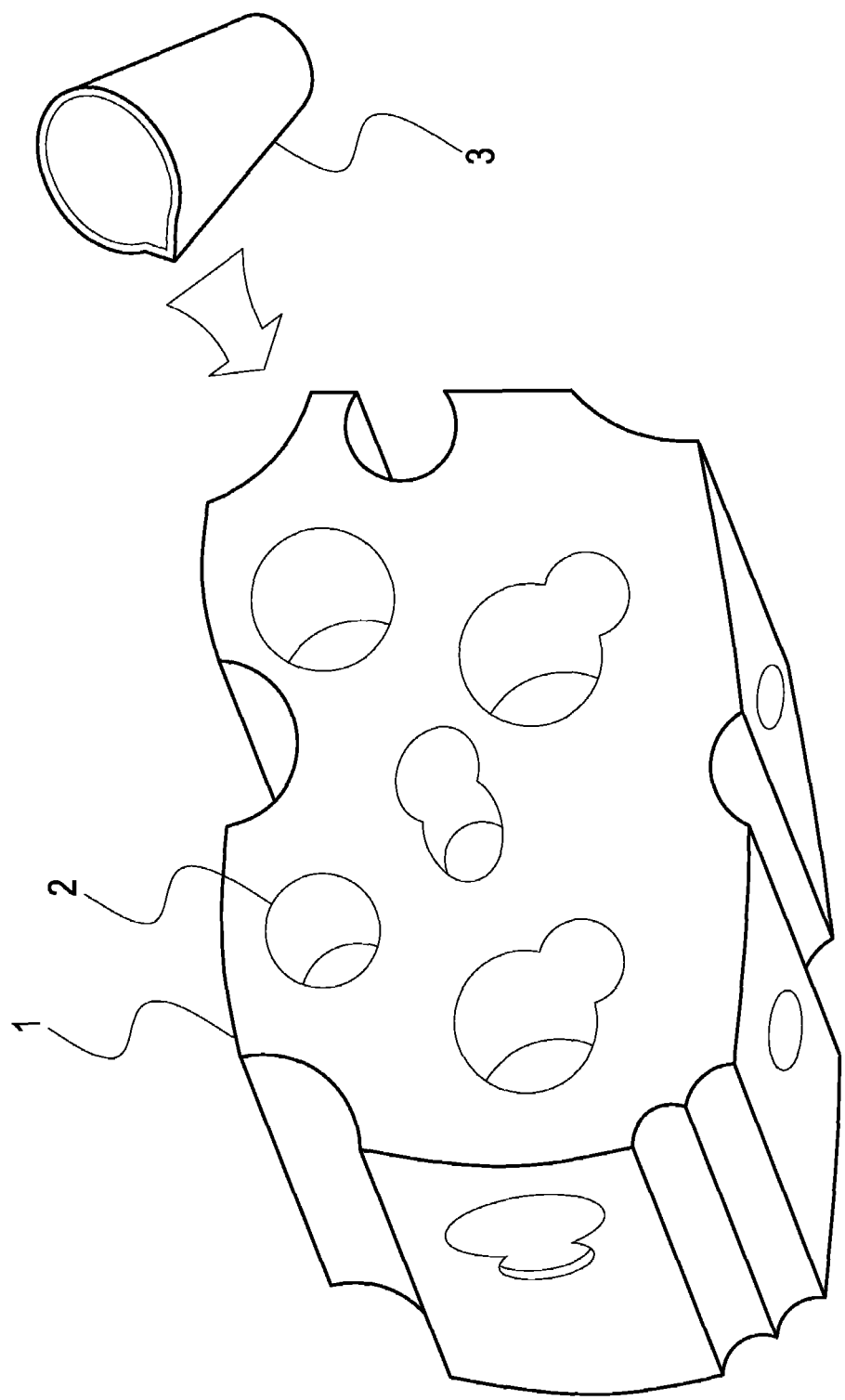
FIG. 2 is a schematic view of porous micro-particles according to the invention.
Figure 3:
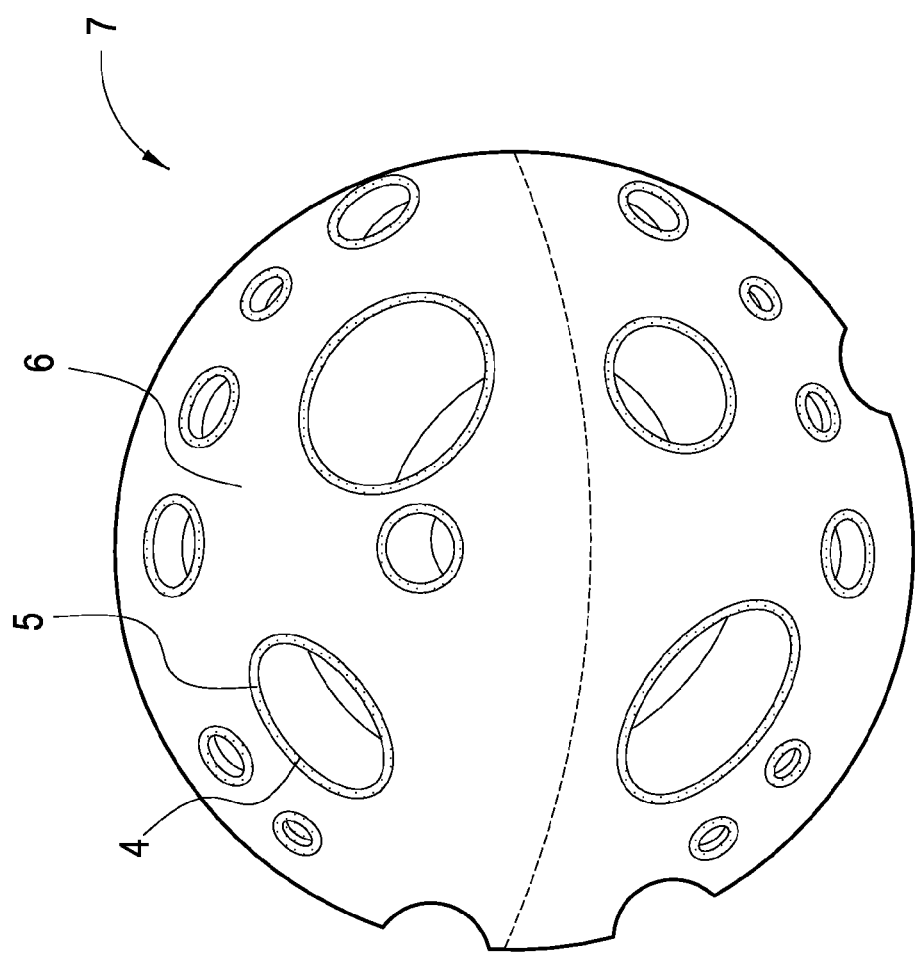
FIG. 3 is a schematic view of finer micro-particles obtained after dry-grinding according to the invention.
Figure 4:
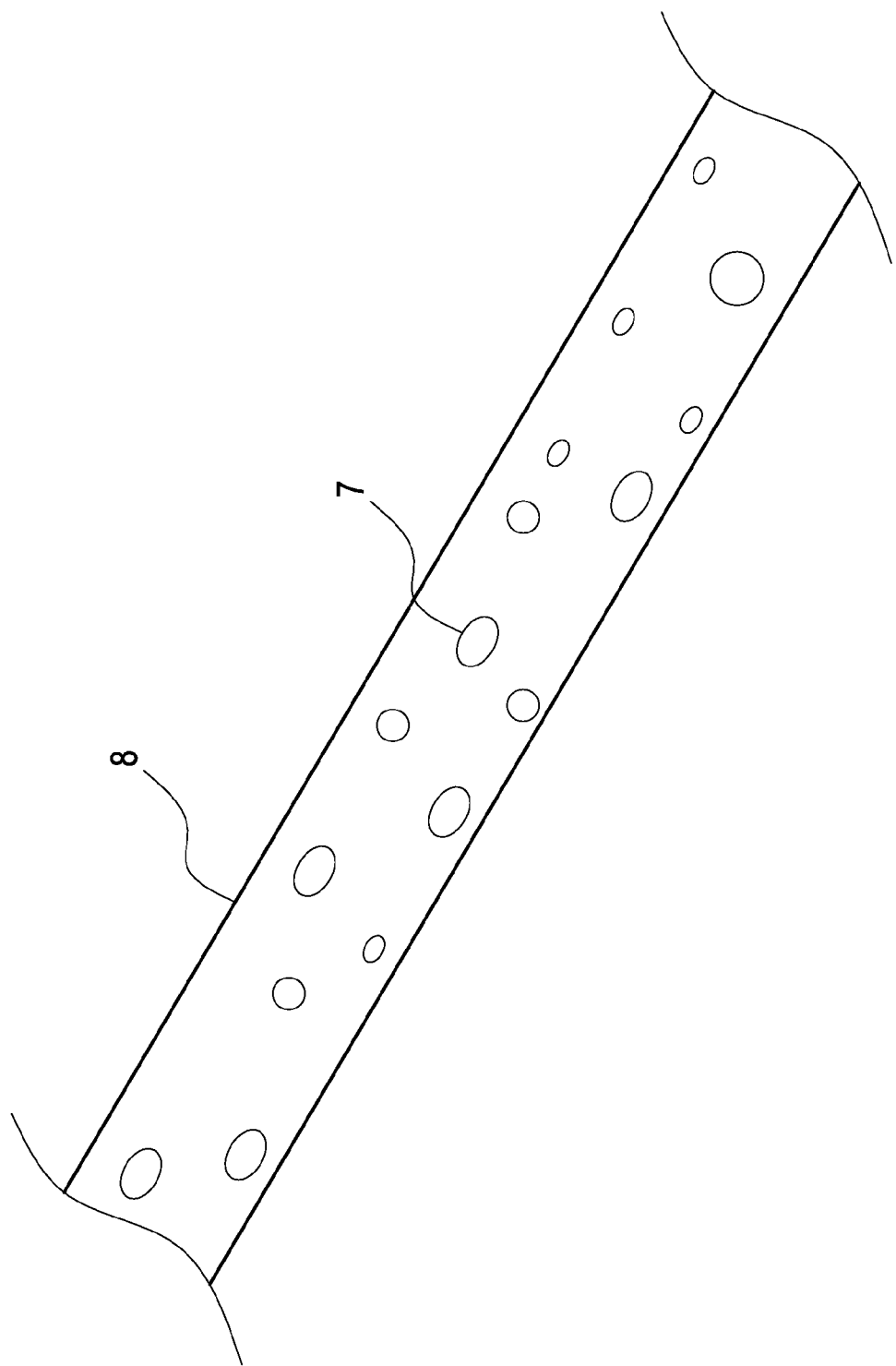
FIG. 4 is a schematic view of anti-bacterial polyester fibers according to the invention.

Referring to FIG. 1, the process for producing porous polymer masterbatch and fiber thereof having anti-bacterial and odor eliminating functions provided according to the invention comprises following steps:

step 1: grinding kieselguhr or active carbon into micro-particles of 1~1000 micron (111);

Referring to FIG. 2, a schematic view of kieselguhr or active carbon micro-particles. In the step 1, kieselguhr or active carbon is ground at first into micro-particles 1. In the case of active carbon, the principal component of active carbon is carbon, combined with minor amount of hydrogen, oxygen, nitrogen, sulfur and the like, and is a black porous material 2 with complex surface. It has a six ring structure formed from carbon and its shape may range from a cylindrical coarse granule to a fine powder particle, and hence it has two type of morphology of granule and powder. The granule has generally a diameter of 1~6 mm, and its length is 0.7~4 times of its diameter. Alternatively, it may be present as a granule of irregular shape with 6~120 particle mesh. The active carbon is odorless, and tasteless, and is insoluble in water and organic solvent. Active carbon has a packing density of about 0.3~0.6 g/ml, a volume of the very large micro-pore of about 0.6~0.8 ml/g, and a specific surface of about 500~1,500 $m^2/g$, and therefore, exhibits a very strong adhesive force to an organic macromolecular material;

In addition, kieselguhr can be used in the process of the invention. Kieselguhr is mined from fossil lake beds. Such kieselguhr is formed from the deposition of large amounts of dead micro-diatoms on the ancient lake or sea bed. Diatom is classified into two morphologies of salt water diatom and fresh water diatom. Accordingly, the thus-mined kieselguhr is classified also into two types; salt water kieselguhr and fresh water kieselguhr. After mining, it can be washed, processed and ground into micro-powder of various specific sizes;

step 2: impregnating micro-particles obtained in step 1 in an organic Chinese herbal medicine and a water-soluble cementing agent, adding inorganic anti-bacterial minerals of 1~100 nm in size, and then stirring continuously for more than 24 hours, thereby enabling the organic Chinese herbal medicine and inorganic anti-bacterial minerals to be impregnated, bound and adhered sufficiently in the pores of the micro-particle (112);

Referring to Table 1, each of the inorganic anti-bacterial minerals mentioned above has its own special effect. Inorganic anti-bacterial minerals used in the process of the invention may be selected from the group consisting of realgar, calamine, melanterite, talc, alum, sulfur, borax, nanometer silver (Ag), nanometer zinc (Zn), nanometer copper (Cu), titanium dioxide ($TiO_2$) and any combination thereof;

TABLE 1

The pharmacological effect, function and chemical component of inorganic anti-bacterial minerals.

| Item | Name | Pharmacological effect |
|---|---|---|
| 1. | Realgar | Detoxification, removing moisture, killing insects, anti-bacterial |
| 2. | Calamine | Absorbing moisture, stopping itch, controlling sores, antiseptic, anti-bacterial |
| 3. | Melanterite | Treating eczema, killing insects, anti-bacterial |
| 4. | Talc | Treating eczema, wet sore, scabies, anti-bacterial |
| 5. | Alum | Detoxification, killing insects, drying moisture, stopping itch, wide spectrum anti-bacterial |
| 6. | Sulfur | Killing insects, stopping itch, scabies, eczema, killing insects, anti-bacterial |
| 7. | Borax | Detumescence, antiseptic, anti-bacterial, treating scabies and itch |
| 8. | Nanometer silver (Ag) | Anti-bacterial, anti-fungal |
| 9. | Nanometer zinc (Zn) | Anti-bacterial, anti-fungal |
| 10. | Nanometer copper (Cu) | Anti-bacterial, anti-fungal |
| 11. | Titanium dioxide ($TiO_2$) | Anti-bacterial, anti-fungal |

The water-soluble cementing agent 3 may be selected from polyvinyl alcohol (PVA) or the like. PVA is an extensively used water-soluble macromolecular polymer, with a property between those of plastic and rubber. Since PVA possesses a strong bonding property, flexibility, smoothness of the surface texture, oil resistance, solvent resistance, protective gel property, gas insulating property, wear resistance and after special treatment, water resistance, it is used very often in raw materials for fiber;

The binding property of PVA is utilized to adhere the extract essence fluid of herbal plants on the surface of the outer and inner holes of micro-particles so as to increase the amount and surface area of the organic Chinese herbal medicine and inorganic anti-bacterial minerals thus-adhered. The herbal plants useful in the process according to the invention may be selected from the group consisting of Radix et RhizomanNotopterygii, Black false hellebore, *Hibiscus syriacus* skin, *Cinnamomum cassia* Presl, camphor, *Cnidium monnieri* (L) Cuss, *Hydnocarpus anthelmintica* Pier., rosin and any combination thereof. Each of the herbal plants mentioned above has its own specific effect as shown in Table 2;

TABLE 2

Pharmacological effect, functions and chemical components of Chinese herbs

| Item | Name | Pharmacological effect | Function | Chemical components |
|---|---|---|---|---|
| 1. | Radix et Rhizoma notopterygii | Anti-bacterial, anti-fungal | | |

TABLE 2-continued

Pharmacological effect, functions and chemical components of Chinese herbs

| Item | Name | Pharmacological effect | Function | Chemical components |
|---|---|---|---|---|
| 2. | Black false hellebore | Anti-bacterial, anti-fungal, killing insects | | |
| 3. | Hibiscus syriacus skin | Killing insects, stopping itch, anti-bacterial | | |
| 4. | Cinnamomum cassia Presl | Anti-bacterial, anti-bacterial anti-tinea, anti-fungal | Sedation, Analgesia, Allaying fever | Cinnamic aldehyde, Cinnamic acid, Cinnamyl acetate, Phenylpropyl acetate |
| 5. | Camphor | Removing moisture, killing insects, anti-bacterial, anti-fungal | | |
| 6. | Cnidium monnieri (L) Cuss | Anti-fungal, anti-Gram negative bacteria, anti-mold Anti-Ringworm fungus | Removing rheumatism, drying moisture, killing insects, stopping itch | L-Piuene, L-Camphene, Bornyl isovalerate, Isoborneol, Edultim, Cnidimine, Xanthotoxin |
| 7. | Hydnocarpus anthelmintica Pier. | Anti-bacterial, treating tinea manus and tinea pedis | Detoxification, killing insects, removing tinea cruris | Chaulmoogric Acid, Hydnocarpic Acid, Gorlic Acid |
| 8. | Rosin | Anti-bacterial, anti-mold, treating scabies, wet itch | | |

The organic Chinese herbal medicine and inorganic anti-bacterial minerals mentioned in step 2 may be used in combination with one another to achieve the desired pharmacological effect and function;

step 3: air drying the micro-particle impregnated in step 2, and dry grinding them further into finer micro-particle of 1~50 micron in size suitable for drawing, and dispersing them homogeneously in a solution (113);

Referring to FIG. 2, the surface and the outside and inside of the holes in the thus-impregnated micro-particles had been adhered with extract essence fluid of the herbal plants. Thereafter, the impregnated micro-particles thus air dried were dry ground further into finer micro-particles. The surface 6 and the outside and inside of holes 4 in the thus-obtained finer micro-particles 7 had been adhered with the organic Chinese herbal medicine and inorganic anti-bacterial minerals 5. The air-dried finer micro-particle 7 had a size of 1~50 micron and became a finer micro-particle suitable for drawing as well as could be dispersed homogeneously in a solution.

The solution mentioned in the step 3 of the inventive process may be ethylene glycol solution. Ethylene glycol is a catalyst used in the condensation polymerization of polyester, and has the following advantages: 1. It has greater solubility and better dispersability in ethylene glycol solution; 2. It has good activity, and can enhance productivity of the apparatus; 3. This catalyst itself will not introduce new contaminants, can increase the intrinsic mass and improve post-processing spinning ability; 4. It can improve hues and heat stability of the slice.

step 4: binding the finer micro-particle dispersed homogeneously in the solution to a monomer through esterification reaction to form anti-bacterial polyester masterbatch, wherein such finer micro-particle in each of the polyester masterbatch comprises about 10-25% of the total weight of each masterbatch (114);

step 5: Using low temperature batch processing chip spinning technique to produce the anti-bacterial polyester masterbatch to produce anti-bacterial polyester fiber 8, wherein the ratio of the anti-bacterial polyester masterbatch added is about 5-10% (115).

In summary, the process for producing porous polymer masterbatch and fiber thereof having anti-bacterial and odor eliminating functions provided by the invention comprises following steps:

step 1: grinding kieselguhr or active carbon into micro-particles of 1~1000 micron in size (111);

step 2: impregnating micro-particles obtained in step 1 with organic Chinese herbal medicine and water-soluble cementing agent and inorganic anti-bacterial minerals of 1~100 micron in size, and stirring continuously for more than 24 hours, thereby enabling sufficient penetration, binding and adsorption of the organic Chinese herbal medicine and inorganic anti-bacterial minerals in pores of micro-particles (112);

step 3: air drying micro-particles impregnated in step 2, and then dry grinding said dried micro-particles into finer micro-particle of 1~50 micron in size suitable for drawing and dispersing homogeneously in a solution (113);

step 4: binding said finer micro-particles dispersed homogeneously in a solution with monomer through esterification reaction to form said anti-bacterial polyester masterbatch, wherein such finer micro-particle in each of the polyester masterbatch comprises about 10-25% of the total weight of each masterbatch (114);

step 5: producing anti-bacterial polyester fiber from said anti-bacterial polyester masterbatch by low temperature batch processing chip spinning technique, wherein the ratio of the anti-bacterial polyester masterbatch added is about 5-10% (115).

Accordingly, the process for producing porous polymer masterbatch and fiber thereof having anti-bacterial and odor eliminating functions provided by the invention has following advantages over other conventional techniques:

1. The inventive process for producing porous polymer masterbatch and fiber thereof having anti-bacterial and odor eliminating functions can reduce the lost amount of particles originally present in the anti-bacterial inorganic solvent, wherein said particles is susceptible to be washed off, and thus, may lower its anti-bacterial effect as well as may cause an unexpected influence on the ecological equilibrium of the environment.

2. The inventive process for producing porous polymer masterbatch and fiber thereof having anti-bacterial and odor eliminating functions can enable these odor eliminating anti-bacterial materials to penetrate and adhere into tremendous micro-pores of these porous particles, and further, since they can bind in these micro-pores by means of water-soluble cementing agent, thereby these materials tend not to lose and hence can achieve the purpose of increasing its anti-bacterial and odor eliminating functions.

3. The inventive process for producing porous polymer masterbatch and fiber thereof having anti-bacterial and odor eliminating functions can be extended to make various related products having anti-bacterial and odor eliminating functions, such as shoes, bags, socks, clothes.

4. The inventive process for producing porous polymer masterbatch and fiber thereof having anti-bacterial and odor eliminating functions can adopt wide and diverse materials, and hence can retain wide spectrum anti-bacterial and anti-fungal effects, without loses its anti-bacterial function during dying and finishing process due to bind with chlorine and sulfur like, for example, using nanometer silver alone.

Many changes and modifications in the above-described embodiment of the invention can, of course, be carried out without departing from the scope thereof. Accordingly, to promote the progress in science and useful arts, the invention is disclosed and is intended to be limited only by the scope of the appended claims.

What is claimed is:

1. A method for producing an anti-bacterial polyester fiber from an anti-bacterial polyester masterbatch, said method comprising:
   a.) grinding active carbon into micro-particles of 1-1000 micron in size;
   b.) impregnating the active carbon micro-particles obtained in a.) with a Chinese herbal medicine selected from the group consisting of Radix et *Rhizoma notopterygii*, Black false hellebore, *Hibiscus syriacus* skin, *Cinnamomum cassia* Presl, Camphor, *Cnidium monnieri* (L) Cuss, and *Hydnocarpus anthelmintica* Pier and Rosin, or a combination thereof, and a water-soluble cementing agent; adding nanometer silver, wherein said nanometer silver is 1-100 nanometers in size to said impregnated active carbon micro-particles and water-soluble cementing agent; and stirring continuously for more than 24 hours, wherein said Chinese herbal medicine and nanometer silver penetrate, bind and adsorb into pores of the active carbon micro-particles;
   c.) air drying the active carbon micro-particles in b.); and dry grinding said dried active carbon micro-particles into finer micro-particles of 1-50 micron in size wherein said finer micro-particles are homogenously dispersed in a solution;
   d.) binding the finer micro-particles dispersed homogeneously in the solution with a monomer through an esterification reaction to form the anti-bacterial polyester masterbatch; and
   e.) producing the anti-bacterial polyester fiber from the anti-bacterial polyester masterbatch using a low temperature batch processing chip spinning technique.

2. The method of claim 1, wherein said water-soluble cementing agent is polyvinyl alcohol.

3. The method of claim 1, wherein said solution is ethylene glycol solution.

* * * * *